United States Patent
Florent et al.

(10) Patent No.: US 8,498,463 B2
(45) Date of Patent: Jul. 30, 2013

(54) MASK CONSTRUCTION FOR CARDIAC SUBTRACTION

(75) Inventors: Raoul Florent, Ville Davray (FR); Vincent Maurice Andre Auvray, Paris (FR); Odile Bonnefous, Rueil-Malmaison (FR)

(73) Assignee: Koninklijke Philips N.V., Eindhoven (NL)

( * ) Notice: Subject to any disclaimer, the term of this patent is extended or adjusted under 35 U.S.C. 154(b) by 247 days.

(21) Appl. No.: 13/058,205

(22) PCT Filed: Aug. 6, 2009

(86) PCT No.: PCT/IB2009/053446
§ 371 (c)(1),
(2), (4) Date: Feb. 9, 2011

(87) PCT Pub. No.: WO2010/018501
PCT Pub. Date: Feb. 18, 2010

(65) Prior Publication Data
US 2011/0305378 A1  Dec. 15, 2011

(30) Foreign Application Priority Data
Aug. 13, 2008 (EP) .................................. 08305472

(51) Int. Cl.
*G06K 9/00* (2006.01)
(52) U.S. Cl.
USPC .......................................................... 382/130

(58) Field of Classification Search
USPC ....... 382/128–134; 128/920–925; 356/39–49; 600/407–414, 424–426; 345/581–618
See application file for complete search history.

(56) References Cited

U.S. PATENT DOCUMENTS

| 4,729,379 | A | 3/1988 | Ohe |
| 4,903,705 | A | 2/1990 | Imamura et al. |
| 2007/0195932 | A1 | 8/2007 | Nakaura et al. |

FOREIGN PATENT DOCUMENTS

| JP | 2006051070 | 2/2006 |
| WO | WO03083777 | 10/2003 |

*Primary Examiner* — Atiba O Fitzpatrick

(57) ABSTRACT

To provide an improved method for achieving DSA images where the effect of residual motions in cardiac DSA during the perfusion phase is reduced and in order to display subtracted images containing less motion artefacts, a method of performing digital subtraction angiography DSA in an imaging apparatus comprises the steps of generating a first image sequence of mask images (10) of a subject to be examined, generating at least one first contrast image (22) at a first phase (16) whereby in the first contrast image part of the subject has a different contrast than in said first image sequence, subtracting the mask images (10) from the at least one first contrast image (22) generating a first DSA image sequence (24), subtracting the DSA images of the first DSA image sequence (24) from the first contrast image (22) within the first phase (16) generating a sequence of extended mask images (32); generating a second contrast image (34) with the imaging system at a second phase (18), said second phase (18) being separated from the first phase (16) by a predetermined phase dividing time limit (20), subtracting the images of the sequence of the extended mask images (32) from the second contrast image (34) generating a second DSA image sequence (38), displaying the second DSA image sequence (38) on a display (28).

11 Claims, 4 Drawing Sheets

MASK CONSTRUCTION FOR CARDIAC SUBTRACTION

FIELD OF THE INVENTION

The invention is related to perfusion procedures in Digital Subtraction Angiography (DSA), especially in cardiac DSA. The invention also relates to an imaging system performing DSA, to a computer program element and to a computer-readable medium.

BACKGROUND OF THE INVENTION

For some examinations of the human body it is of great advantage to image only the blood vessels. One known method for this is subtraction angiography, which is based on a perfusion procedure. Basically, a first and a second image are acquired of a region of interest. Between the two images a contrast medium is introduced into the blood vessel, which absorbs X-rays. After the contrast agent is injected an X-ray imaging device records an angiographic sequence that shows the blood vessels containing the contrast agent highlighted in the X-ray image. In order to make the vessel, and especially in heart investigations the myocardial information, more accessible to the clinician, its visibility is improved. Therefore, the two images are subtracted from one another. In theory, as a result only the vascular tree filled with the contrast agent is visible. This procedure is called Digital Subtraction Angiography (DSA) in case the subtraction is done on a digital basis. DSA images are used for diagnosis and intervention purposes among others. DSA is today routinely used in vascular exams or interventions where the observed vascular structures do not move (example: in the legs, brain, etc. . . . ). But it has shown, that motion of the object between the acquisition of the first and the second image leads to disturbing artefacts in the DSA image, as background structures can only be completely eliminated where these structures are exactly aligned and have equal grey-level distributions. Its sensitivity to motion that could have occurred between the current injected frame and the corresponding mask frame (the so-called residual motion, due to heartbeat or respiration for example) is a serious disadvantage of the technique. For example, in heart investigations, patients with heavy cardiac disease ordinarily undergo cardiac catheterization. This inspection clarifies the degree of coronary stenoses and aneurism size. However, it is impossible to clarify myocardial perfusion (which is the ultimate goal of the exam) from the coronary shape. The reason is that once stenoses occur, the other normal coronaries begin to provide the ischemic muscle with blood. As a result, there is scarcely any relation between the coronary shape and myocardial perfusion. Hence, an exact image of the actual blood vessels and of the perfused regions is necessary. But the motion of the heart leads to artefacts on the DSA images.

In U.S. Pat. No. 4,729,379 the use of images corresponding to one cardiac cycle is proposed to reduce the amount of disturbing artefacts. The subtraction is performed between images of the same cardiac beat phase, thereby removing image components due to the cardiac beat from the subtraction image. In US 2007/0195932 A1 a method is described where a non-contrast region is detected in both image sequences as a reference and a mask image is selected showing the minimal positional shift in relation to the current target image. A method of eliminating motion-artefacts in X-ray imaging processes by synchronizing the radiographing of the live image, i.e. the target image, and the mask image with the heartbeat is foreseen in U.S. Pat. No. 4,903,705. The document JP 2006-051070 shows a method for improving a DSA process by automatically choosing an optimal mask image for the creation of a DSA picture, which is done by providing a so-called phase contrast evaluation function using human body analytical data for selecting a mask image that shows the smallest difference to the target image. Further, WO 03/083777 A2 describes a method where the image sequences are aligned by using reference signs, i.e. motion signals, which are examined by the means of a similarity function to determine two instants at which the object has approximately the same state of motion during the respective motions. When dealing with non-cardiac DSA (mostly neurological, anterior or posterior limb exams), residual motions mostly come from global patient motions. The resulting artefacts can be corrected to some extent by digitally compensating for the motion that has occurred between the mask image and the currently injected image. But residual motions observed in cardiac DSA appear more often, with larger amplitudes, and they are more difficult to compensate for (compared to non-cardiac DSA). This is mainly because the beating of the heart varies in pace, rhythm and amplitude, in particular when a contrast agent is injected. It is then difficult to find a matching pair of images to apply subtraction. Further, breathing could also impair the mask/injected frame matching and it is more difficult to hold its breath during an exam than to simply stay motionless. Still further, perfusion exams of the heart last longer than classical angiography exams since not only the contrast agent has to propagate in the vessels (during the arterial phase) of interest, but one has to wait for the subsequent migration of the contrast agent in the heart muscle (during the perfusion phase). This results in much longer exams (10-15 seconds vs. 2-4 seconds), which also implies more frequent and larger residual motions. Another aspect is that X-ray images are transparent. That makes the estimation and compensation of the organs that they contain particularly difficult. Indeed, if organ 1 moves over organ 2, one could either compensate for the motion of organ 1 (and thus to move artificially organ 2), or to leave the artefact created by the motion of organ 1. Non-cardiac DSA mainly needs to correct for global patient motions that do not imply any transparency effect. On the contrary, cardiac exams do involve strong transparent effects (lungs, diaphragm, heart, column and ribs can move over each other, with superimposed, possibly contradictory, vector fields). As a result, it is much more difficult to compensate for residual motions in cardiac DSA than in non-cardiac DSA. But it is crucial to limit the artefacts corrupting the subtracted images presented to the clinician as much as possible.

SUMMARY OF THE INVENTION

The object of the invention is to provide an improved method for achieving DSA images in which the effect of residual motions during the perfusion phase is reduced in order to display subtracted images containing less motion artefacts.

The object is reached with a method of performing digital subtraction angiography DSA in an imaging apparatus, comprising the steps of generating a first image sequence of mask images of a subject to be examined; generating at least one first contrast image at a first contrast phase whereby in the first contrast image a part of the subject has a different contrast than in said first image sequence, subtracting the mask images from the at least one first contrast image generating a first DSA image sequence, subtracting the DSA images of the first DSA image sequence from the first contrast image within the first phase generating a sequence of extended mask images; generating a second contrast image at a second phase, said second phase being separated from the first phase by a predetermined phase dividing time limit, subtracting the images of the sequence of the extended mask images from the second contrast image generating a second DSA image sequence and displaying the second DSA image sequence on a display.

One of the advantages of the invention is that by providing the extended mask image as an additional image, the (residual) motions that have occurred at the first contrast phase, which for example may include an introduction of a contrast medium, will be taken into account in the new mask and will not have to be compensated for during the perfusion phase. This means, that artefacts will arise only from motions that have occurred between the end of the first phase and the considered frame in the second phase. In contrast to this, in common DSA procedures artefacts are caused by motions that occur right after the end of the mask acquisition, which is at the beginning of the contrast introduction phase and not only in the second half of the latter. Reducing the time between the current frame and the frames used to build the mask effectively reduces the occurring of artefacts. Of course any known method can be used for further image correction. As an effect, a new object that is introduced in the field of view during the first phase and that is removed before the second phase starts, appears repeatedly on the display during the second phase. For example, the repeated appearance can be made visible by reverse video or the like, as the image displayed after the second DSA, i.e. after the third subtraction, does not show said object. The repeated appearance of such an object is a clear indication that first phase images were involved in the creation of the mask during the second phase subtraction. With conventional DSA an object introduced after the initial mask images would appear on the displayed image after the DSA, i.e. on the final image(s).

In a preferred embodiment of the method the DSA method is a cardiac DSA method, because these are very crucial concerning disturbing artefacts due to residual motion.

In another preferred embodiment the first phase is an arterial phase of the contrast phase, the second phase is a perfusion phase of the contrast phase and the phase dividing time limit is a coronary time limit. Preferably the arterial phase limit is defined by means of image-based criteria. Usually, in perfusion the contrast medium first enters the vessels to be examined in a rather well-defined spatial region. This phase is known as the arterial phase of the contrast injection. When the perfusion progresses the contrast medium migrates towards the myocardiac muscle, yielding a larger and more diffuse spatial region which exists for a further time period. This phase is called the perfusion phase of the contrast injection. Performing the process according to these phases has the advantage that the first subtracted DSA images contain only the coronary arteries and it is unlikely that any serious artefacts are present in these images. Since little time has passed between the end of the mask acquisition and the acquisition of the first contrast images, approximately 0 to 4 seconds, little residual motion is present on these images. It is therefore easy to compensate for those slight discrepancies. Additionally, the contrast medium trajectory is well-defined during the arterial phase. This is not the case during the perfusion phase. Hence, the images generated in the first phase produce easily identified objects. As a result, at that point it is often easier to compensate for artefacts than during the perfusion phase. This leads to mostly artefact-free subtraction images.

In a preferred embodiment the extended mask image sequence is chronologically closer to the second contrast image than the mask image sequence. With regard to common investigation timing a method is preferred wherein the extended mask image sequence is 2 to 4 seconds closer to the second contrast image than the mask image sequence. The gain in the mask-to-current-image time results in a major reduction of the extent of the potential residual motions (and for the corresponding reduction of transparency artefacts), yielding a much better subtraction quality. Of course the invention is compatible with any existing cardiac DSA method and also any motion compensation technique.

Preferably, in one embodiment the determination of the introduced phases (arterial and perfusion phases) is automatically determined and does not require patient specific settings. There is a variety of ways to achieve this goal. One might rely on fixed time values, or fixed number of heart cycles (or the combination of both), or even on image-based detection. In addition, the use of an electronic and programmable contrast-agent injector might facilitate this determination (for instance the injection might accurately start after a programmed time period following the sequence acquisition start). One might also use a combination of those methods. For instance, the arterial phase can be automatically detected by digitally monitoring the contrast in the image content, and the perfusion phase can be set with a fixed time interval (or a fixed number of heart cycles, or a fixed combination of both) separating it from the automatically detected arterial phase start).

Preferably, in one embodiment the first DSA image sequence is being displayed on a display before displaying the second DSA image sequence to provide this information to the clinician. In case of special requirements such as quality control it is further provided, to display both the first DSA image sequence and the second DSA image sequence parallel to each other.

According to the invention, the object is also reached with an imaging system for performing digital subtraction angiography DSA that comprises an image generating device, a processing unit and a display. The processing unit is arranged to receive data of a first image sequence of mask images and data of at least one first contrast image from the image generating device and to generate a first DSA image sequence, to subtract the first DSA images from the first contrast image to generate extended images and to subtract the extended images from second contrast images to generate a second DSA sequence. The display is arranged to display the second DSA images.

According to a further exemplary embodiment of the present invention, a computer program element is provided that is characterized by being adapted to perform the steps of the method according to one of the preceding embodiments.

This computer program element might therefore be stored on a computing unit, which might also be part of an embodiment of the present invention. This computing unit may be adapted to perform or induce the performing of the steps of the method described above. Moreover, it may be adapted to operate the components of the above described-X-ray imaging system. The computing unit can be adapted to operate automatically and/or to execute the orders of a user.

This embodiment of the invention covers both a computer program, that right from the beginning uses the invention, and a computer program, that by means of an update turns an existing program into a program that uses the invention.

Further on, the computer program element might be able to provide all necessary steps to fulfill the procedure of representing blood flow-related information in X-ray images as described above.

According to a further embodiment of the present invention, a computer-readable medium is presented wherein the computer-readable medium has a computer program element stored on it which computer program element is described by the preceding section.

According to a further embodiment of the present invention, a medium for making a computer program element available for downloading is provided, which computer program element is arranged to perform the method according to one of the previously described embodiments of the invention.

These and other aspects of the invention will be apparent from the embodiment described hereinafter with reference to the drawings.

DETAILED DESCRIPTION OF EMBODIMENTS

Figure 1:
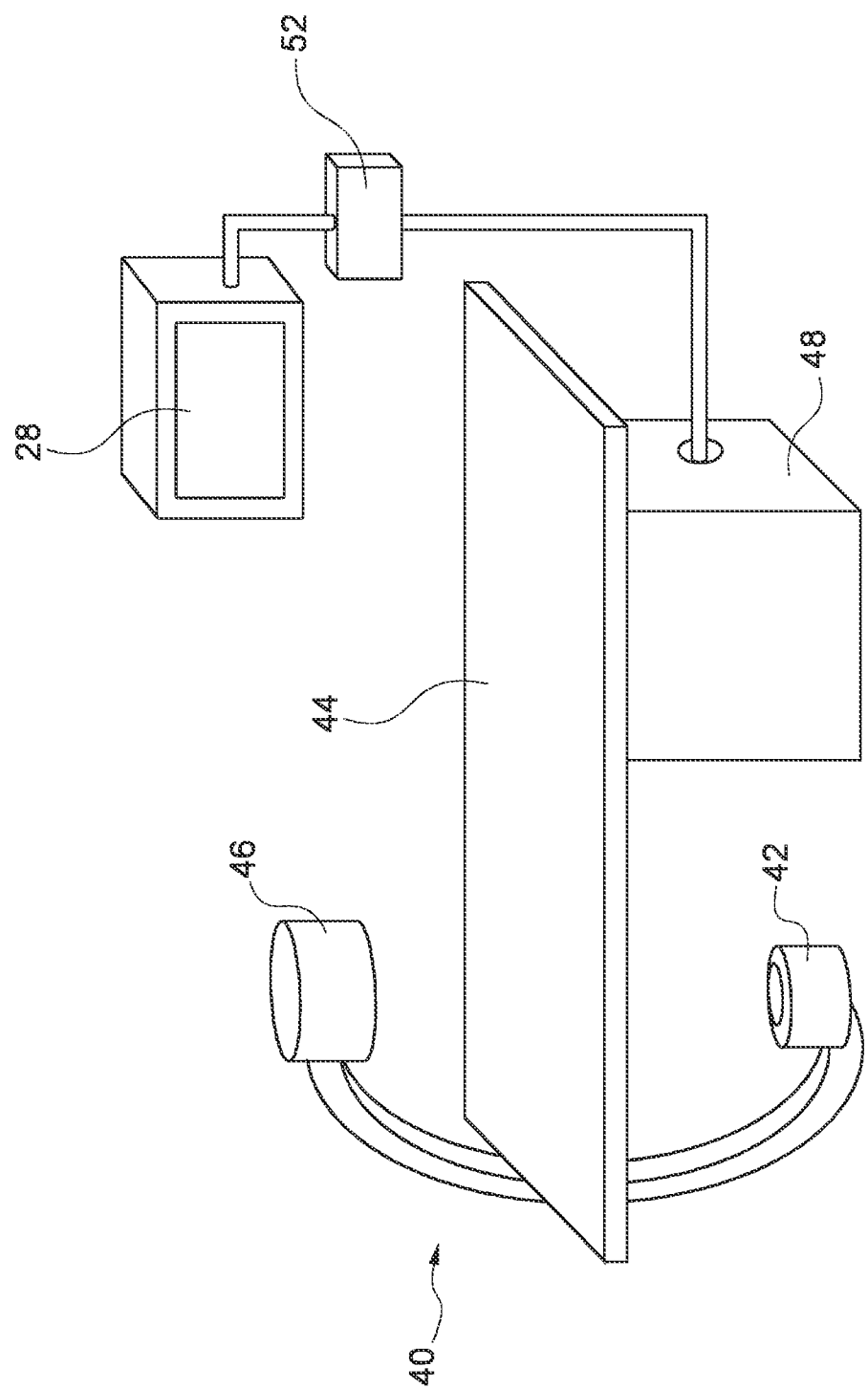
FIG. 1 schematically describes an X-ray imaging device according to the invention.

FIG. 1 schematically shows an X-ray imaging system 40. A source of X-ray radiation 42 is provided to generate X-ray radiation. A table 44 is provided to receive a subject to be examined. Further, an X-ray image detection module 46 is located opposite the source of X-ray radiation 42, i.e. during the radiation procedure, the subject is located between the source of X-ray radiation 42 and the detection module 46. The latter is sending data to a data processing unit 48, which is connected to both the detection module 46 and the radiation source 42. Furthermore a display 28 is arranged in the vicinity of the table 44 to display information to the person operating the X-ray imaging system, i.e. a clinician. Preferably the display 28 is movably mounted to allow for an individual adjustment depending on the examination situation. Also, an interface unit 52 is arranged to input information by the user. Basically, the image detection module 46 generates images by exposing the subject to X-ray radiation that are further processed in the data processing unit 48. It is noted that the example shown is of a so-called C-type X-ray imaging system. Of course, the invention also relates to other types of X-ray imaging devices. The procedure according to the invention is described in more detail below.

Figure 2:
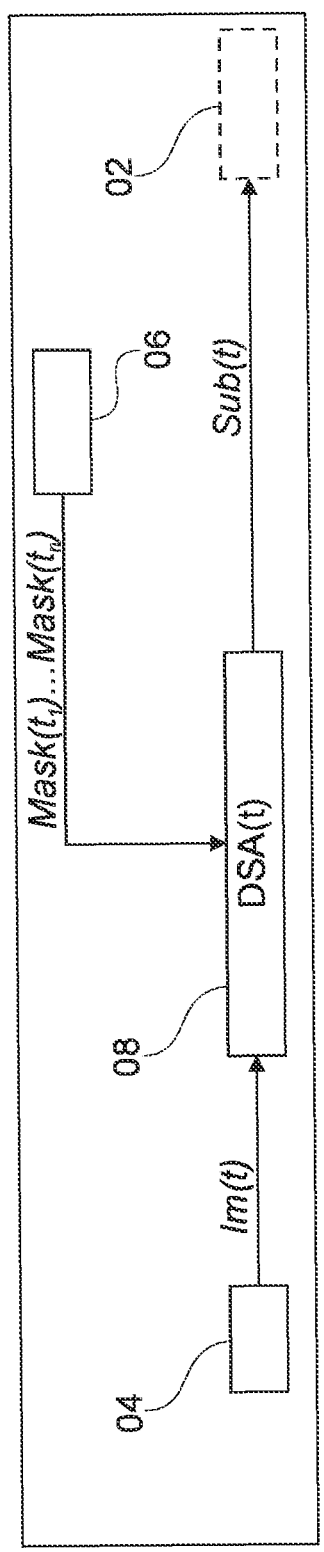
FIG. 2 schematically shows a typical DSA framework of a common DSA procedure according to prior art.

FIG. 2 shows the typical framework of a common DSA method according to prior art where a subtracted image Sub (t) 02 is produced at time t, based on the measured current image at that time Im(t) 04 and a set of mask images Mask($t_l$) . . . Mask($t_n$) 06. The current image 04 is produced during the contrast phase, which for example may include the introduction of a contrast agent, whereas the mask images 06 are acquired before the introduction. The subtracted image 02 is achieved by subtracting the respective mask image from the current image in a DSA procedure 08:

$$Sub(t)=DSA(Im(t),Mask(tl) \ldots Mask(m),t).$$

Of course it is possible that different DSA methods are used along the exam, which explains the dependency to time t in the DSA(.) function: DSA(.)=DSA(.,t).

Figure 3:
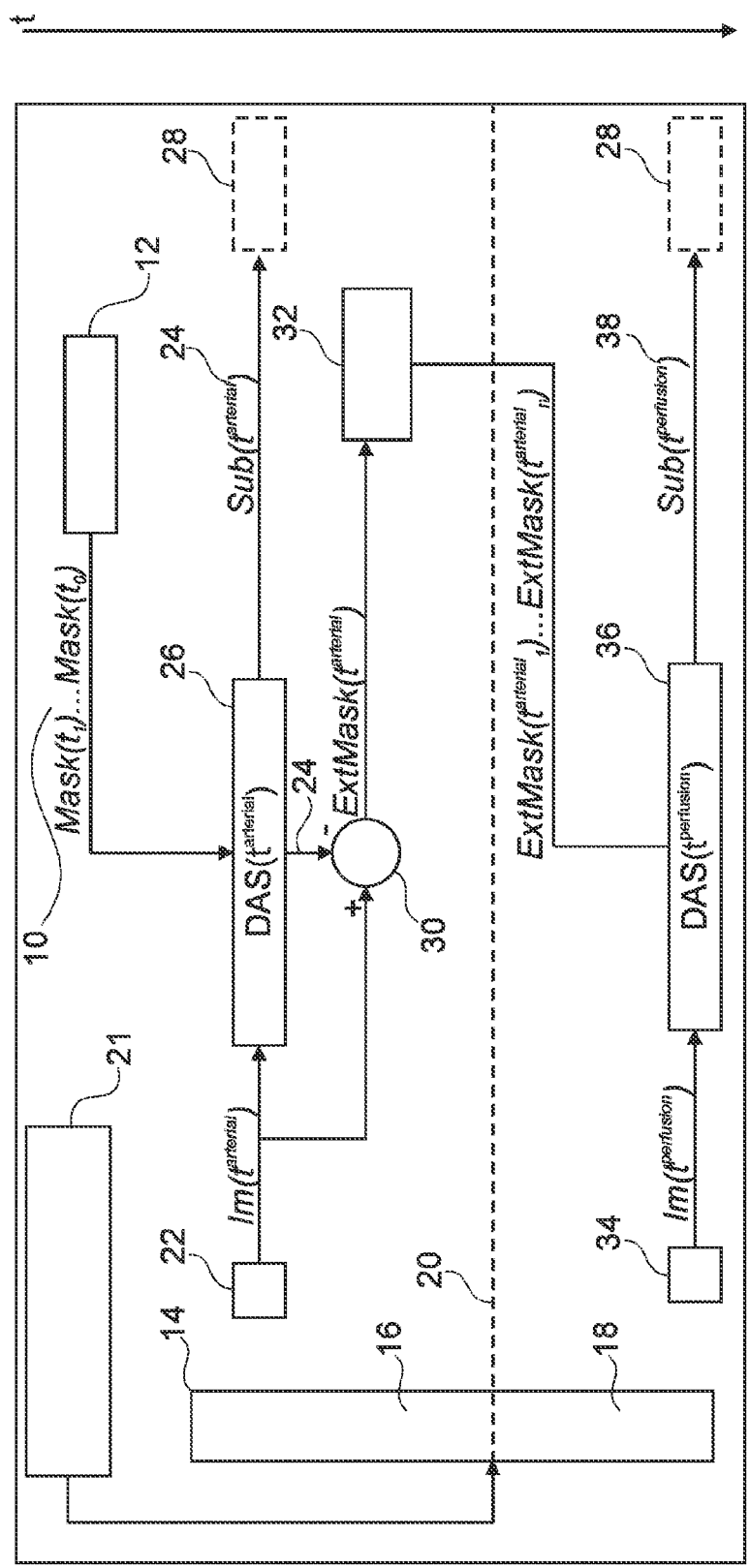
FIG. 3 schematically shows a framework of the method according to the invention.

According to the invention, a method is provided to achieve better subtraction results, said method being schematically shown in FIG. 3. The diagram is displayed chronologically, time elapsing starting at the top of drawing.

In a first step, a first image sequence of mask images 10 of a subject to be examined is generated in a mask image acquisition step 12 with an imaging system. Then a contrast medium is introduced into the subject in a contrast introduction procedure 14.

The contrast phase, for example a contrast introduction procedure 14, is divided into a first phase 16 and a second phase 18 by a phase dividing time limit 20. In perfusion, the state when the contrast medium first enters the vessels to be examined with a rather low concentration is known as the arterial phase of the contrast injection. During further perfusion the concentration of the contrast rises to a maximum which prevails for a further time period. This phase is known as the perfusion phase of the contrast injection 14. According to the invention, it is preferred to use this separation for the first phase 16 and the second phase 18. Accordingly the phase dividing time limit 20 is then a coronary time limit. As the method needs to know when the arterial phase has ended ($t_c$), the time limit 20 is predetermined in a determining step 21 before. The time limit 20 is preferably set according to the perfusion of the contrast medium. This limit can be set based on physical studies (since it depends on an anatomical process), and set once for all. Another possibility provided is to use image-based criteria to define $t_c$.

In a very user-friendly embodiment the determination of the introduced phases is automatically determined, for example by relying on fixed time values, or fixed number of heart cycles or the combination of both. Further, it is also foreseen to use an electronic and programmable contrast-agent injector that facilitates this time phase determination. In a combined embodiment, the arterial phase can be automatically detected by digitally monitoring the contrast in the image content, and the perfusion phase can be set with a fixed time interval separating it from the automatically detected arterial phase start.

After introducing the contrast medium at least one first contrast image 22 is generated (see FIG. 4, left part) with the imaging system during the first phase 16 of the contrast introduction 14. The sequence is generated using an image index $t^{arterial}$. But unlike the time index $t_c$ that is a single instant the index $t^{arterial}$ is a sort of "running" image index under the condition that $t < t_c$.

The at least one first contrast image 22 is used for generating a first DSA image sequence 24 in a first subtraction procedure 26, which is a DSA procedure, where the mask images 10 are subtracted from the first contrast image 22 producing the first DSA image sequence 24. This first subtraction procedure 26 is performed as a regular DSA:

$$Sub(t^{arterial})=DSA(Im(t^{arterial}), Mask(t_l) \ldots Mask(t_n),t^{arterial})$$

The result, i.e. the subtracted DSA images of the first DSA image sequence 24, is displayed on the display 28.

Figure 4:
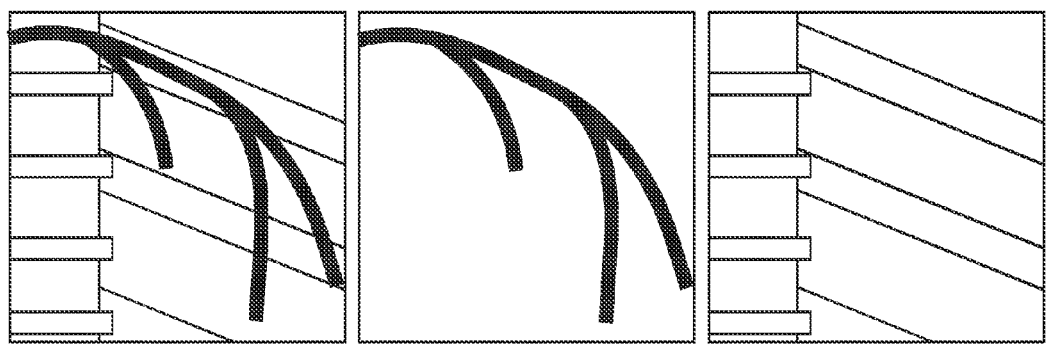
FIG. 4 schematically shows the images corresponding to the method shown in FIG. 3, wherein the left part shows a first contrast image acquired in the first phase, the center part the result of a first DSA step and the right shows the corresponding extended mask to be used for a second DSA step.
Figure 4A:
FIG. 4a shows the images corresponding to the drawings in FIG. 4.

The subtracted DSA images 24 contain the coronary arteries only (see FIG. 4, center part). It is unlikely that any serious artefacts are present in these images Sub($t^{arterial}$) 24. Indeed, little time has passed between the end of the mask acquisition 12 and the acquisition of the first contrast images 22, approximately 0 to 4 seconds, so that little residual motion is present on these images 24. It is therefore easy to compensate for those slight discrepancies.

Moreover, the contrast medium trajectory is well-defined during the arterial phase 16, as opposed to the diffusion observed during the perfusion phase 18, and produces easily identified objects. It is therefore often easier to compensate for artefacts at that point than during the perfusion phase 18, yielding artefact-free subtraction images $\text{Sub}(t^{arterial})$ 24. On the other hand, the first contrast image 22, i.e. the live image $\text{Im}(t^{arterial})$ 12, contains the overall anatomy (heart and background) and the contrast coronary arteries.

The subtracted DSA images 24 are further subtracted from the at least one first contrast image 22 in a second subtraction procedure 30. This second subtraction procedure 30 generates a sequence of extended mask images 32:

$$\text{ExtMask}(t^{arterial}) = \text{Im}(t^{arterial}) - \text{Sub}(t^{arterial})$$

These new images 32 contain the anatomy without the contrast coronary arteries (see FIG. 4, right part). So far, all steps are accomplished during the first phase of the contrast introduction. In other words, by introducing this step into the process, a new mask representing the anatomy only is achieved, the so-called "extended mask" 32, at time $t^{arterial} (>t_n)$.

Then the time limit 20 is passed and the contrast introduction 14 is now within the second phase 18. During this second phase 18 at least one second contrast image 34 is generated with the imaging system.

In a third subtraction procedure 36 the sequence of extended mask images 32 is subtracted from at least one second contrast image 34. This third subtraction procedure 36 is a DSA procedure generating a second DSA image sequence 38. Concerning the time index $t^{perfusion}$ is equivalent to t, with $t > t_c$. A regular DSA is performed, with the difference that the original mask images $\text{Mask}(t_j)$ 10, which are taken before the injection, are substituted with the extended mask images $\text{ExtMask}(t^{arterial})$ 32:

$$\text{Sub}(t^{perfusion}) = \text{DSA}(\text{Im}(t^{perfusion})$$
$$\text{ExtMask}(t^{arterial}_1) \dots$$
$$\text{ExtMask}(t^{arterial}_n), t^{perfusion})$$

Finally the images of the second DSA image sequence 38 are displayed on the display 28. As the extended mask images 32 are temporally closer (typically 2 to 4 seconds) to the considered perfusion image, i.e. the second contrast image 34, less residual motion will be involved, resulting in better displayed subtracted images 38.

The second DSA image sequence 38 can be displayed parallel to the first DSA image sequence 24 so the clinician is provided with two different sequences. But it is also possible to replace the first DSA image sequence 24 on the display 28 with the second DSA image sequence 38 in order to show only one image to the clinician to simplify the information communication. Of course the second DSA image sequence 38 can also be displayed on a further display. For special requirements, such as quality control or setup of the apparatus or for other reasons it is possible to display the entire subtraction sequence at all phases, which is of course also possible next to the display of the non-subtracted sequence.

Several other embodiments are possible. Of course, the extended mask images 32 that are produced in the second subtraction procedure 30 can be performed in many other ways. It could be any function of the mask images 32 and the arterial phase images, i.e. the first contrast images 22:

$$\text{ExtMask}(t^{arterial}) = f(\text{Im}(t^{arterial}_1) \dots \text{Im}(t^{arterial}_m),$$
$$\text{Mask}(t_j) \dots \text{Mask}(t_n), t^{arterial})$$

The subtraction in the perfusion phase 18, i.e. the third subtraction 36, can be a function of the original mask images 10 as well:

$$\text{Sub}(t^{perfusion}) = \text{DSA}(\text{Im}(t^{perfusion}),$$
$$\text{ExtMask}(t^{arterial}_1) \dots \text{EXtMaSk}(t^{arterial}_n),$$
$$\text{Mask}(t_j) \dots \text{Mask}(t_n), t^{perfusion})$$

Extended masks 32 can be built during the perfusion phase 18 as well. They could be computed and used for subsequent subtractions continuously all along the sequence.

In FIG. 4 the images corresponding to the method shown by the drawings in FIG. 3 and which method has been described above, are displayed for a better understanding. The left part shows an example of the first contrast image 22 acquired in the first phase 16 of the contrast introduction 14. The center part shows the result of the first DSA step 26, i.e. the subtracted DSA images of the first DSA image sequence 24. Finally, the right part of FIG. 4 shows the corresponding extended mask 32 to be used for the third subtraction procedure 36, i.e. the second DSA step in FIG. 3.

Figure 5:
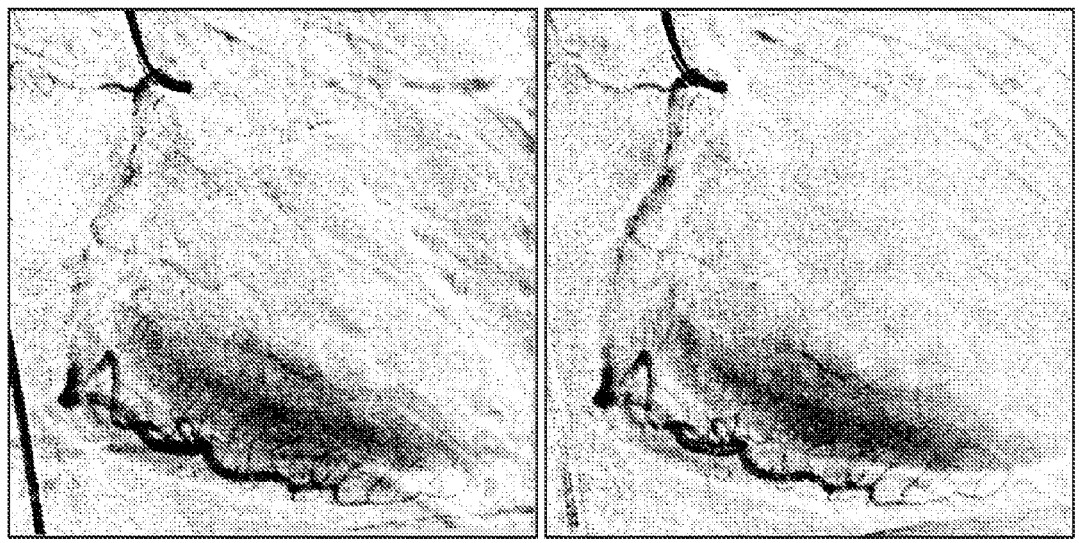
FIG. 5 shows a DSA result without extended mask in the left part and the result with extended mask during the perfusion phase in the right part. Except for the use of an extended mask, two exact similar DSA methods were used in both these cases.

FIG. 5 shows two different DSA results. In the left part a DSA result is shown that has been generated without the use of an extended mask. The right part shows a DSA result according to the invention for which the extended masks were used during the perfusion phase. For comparison reason the same DSA method was used in both cases. As can be seen, the background is much flatter on the right, and the perfusion basin is more clearly defined. Hence, the right part provides the operator, i.e. the clinical staff, with information in such a way that the items of interest can be perceived easier and faster which is crucial for the acceptance of the method provided.

By providing extended mask images 32 during the arterial phase 16 that will be used as a reference subtraction mask during the perfusion phase 18, the residual motions impairing the cardiac DSA are reduced, yielding better displayed subtraction results, during the perfusion phase 18. Hence, the method according to the invention enables a better diagnosis for cardiologists and also an improved possibility of documenting it clearly. In particular, the improved visualisation of the perfused cardiac areas enhances the diagnosis abilities of cardiac DSA. The invention is compatible with any cardiac DSA method. Preferably the invention is to be used by an imaging system for PCI (Percutaneous Coronary Intervention) in catheter laboratories or simply in angiography procedures, to help for diagnosis.

While the invention has been illustrated and described in details in the drawings and forgoing description, such illustration and description are to be considered illustrative or exemplary and not restrictive; the invention is not limited to the disclosed embodiments.

The invention claimed is:

1. A method of performing digital subtraction angiography DSA in an imaging apparatus, comprising the steps of:
   generating a first image sequence of mask images of a subject to be examined,
   generating at least one first contrast image at a first contrast phase whereby in the first contrast image a part of the subject has a different contrast than in said first image sequence,
   subtracting the mask images from the at least one first contrast image generating a first DSA image sequence,
   subtracting the DSA images of the first DSA image sequence from the first contrast image within the first phase generating a sequence of extended mask images, generating a second contrast image at a second contrast phase, said second phase being separated from the first phase by a predetermined phase dividing time limit, subtracting the images of the sequence of the extended mask images from the second contrast image generating a second DSA image sequence, and displaying the DSA images of the second DSA image sequence on a display.

2. A method according to claim 1, wherein the DSA method is a cardiac DSA method.

3. A method according to claim 2, wherein the first phase is an arterial phase of the contrast phase, the second phase is a perfusion phase of the contrast phase and the phase dividing time limit is a coronary time limit.

4. A method according to claim 3, wherein the arterial phase limit is defined by the means of image-based criteria.

5. A method according to claim 3, wherein the arterial phase limit is automatically determined.

6. A method according to claim 3, wherein the extended mask image sequence is chronologically closer to the second contrast image than the mask image sequence.

7. A method according to claim 6, wherein the extended mask image sequence is 2 to 4 seconds closer to the second contrast image than the mask image sequence.

8. A method according to claim 1, wherein the first DSA image sequence is being displayed on a display before displaying the second DSA image sequence.

9. A method according to claim 8, wherein both the first DSA image sequence and the second DSA image sequence are being displayed parallel to each other.

10. An imaging system for performing digital subtraction angiography DSA comprising an image generating device, a processing unit and a display, wherein the processing unit is arranged to receive data of a first image sequence of mask images and data of at least one first contrast image from the image generating device and to generate a first DSA image sequence, to subtract the first DSA images from the first contrast image to generate extended images; and to subtract the extended images from second contrast images to generate a second DSA sequence;

and wherein the display is arranged to display the second DSA images.

11. A non-transitory, computer readable medium comprising a computer program which, when being executed by a processing unit, is adapted to carry out the method of claim 1.

* * * * *